United States Patent
Rizzi et al.

(10) Patent No.: US 11,169,115 B2
(45) Date of Patent: Nov. 9, 2021

(54) METHODS FOR ACCURATE TEMPERATURE MEASUREMENT ON GMR BIOSENSOR ARRAYS

(71) Applicant: The Board of Trustees of the Leland Stanford Junior University, Palo Alto, CA (US)

(72) Inventors: Giovanni Rizzi, Copenhagen (DK); Shan X. Wang, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 346 days.

(21) Appl. No.: 15/968,204

(22) Filed: May 1, 2018

(65) Prior Publication Data

US 2018/0313789 A1    Nov. 1, 2018

Related U.S. Application Data

(60) Provisional application No. 62/659,402, filed on Apr. 18, 2018, provisional application No. 62/492,617, filed on May 1, 2017.

(51) Int. Cl.
*G01N 27/74* (2006.01)
*G01N 33/58* (2006.01)
(Continued)

(52) U.S. Cl.
CPC ......... *G01N 27/745* (2013.01); *C12Q 1/6816* (2013.01); *C12Q 1/6825* (2013.01);
(Continued)

(58) Field of Classification Search
CPC .. G01N 27/745; G01N 33/587; C12Q 1/6816; C12Q 1/6825; G01K 7/16; G01R 33/093
See application file for complete search history.

(56) References Cited

U.S. PATENT DOCUMENTS 6,106,777 A    8/2000  Fujita et al.
8,405,385 B2   3/2013  Hall et al.
(Continued)

OTHER PUBLICATIONS

Guay, Nathan G., et al. "Improving module temperature measurements using averaging resistive temperature devices." 2016 IEEE 43rd Photovoltaic Specialists Conference (PVSC). IEEE, 2016. (Year: 2016).*

(Continued)

*Primary Examiner* — Robert J Eom
(74) *Attorney, Agent, or Firm* — Lumen Patent Firm (57) ABSTRACT

Improved temperature measurement and correction is provided for magnetoresistive sensor arrays. A linear coefficient of resistance vs. temperature is determined from one or more reference sensors in the array by measuring resistance of the reference sensors at known temperatures, which enables resistance measurements to be used to determine unknown temperatures in all sensors of the array. Double modulation leads to MR sensor outputs having center tones which can be used to correct temperature dependence in side tone MR signals. This correction can be according to a linear fit or a polynomial fit. Applications include biological assays requiring accurate temperature data, such as accurate determination of DNA melting curves.

12 Claims, 7 Drawing Sheets

(51) Int. Cl.
*C12Q 1/6825* (2018.01)
*C12Q 1/6816* (2018.01)
*G01R 33/09* (2006.01)
*G01K 7/16* (2006.01)

(52) U.S. Cl.
CPC ............. *G01K 7/16* (2013.01); *G01N 33/587* (2013.01); *G01R 33/093* (2013.01)

(56) References Cited

U.S. PATENT DOCUMENTS

| | | | |
|---|---|---|---|
| 2005/0129090 A1* | 6/2005 | Sheperek | G11B 5/5565 374/185 |
| 2010/0231203 A1* | 9/2010 | Hall | B82Y 25/00 324/202 |
| 2010/0231213 A1 | 9/2010 | Nieuwenhuis et al. | |
| 2016/0161343 A1 | 6/2016 | Smith et al. | |

OTHER PUBLICATIONS

Rizzi, Giovanni, et al. "Denaturation strategies for detection of double stranded PCR products on GMR magnetic biosensor array." Biosensors and Bioelectronics 93 (2016): 155-160. (Year: 2016).*
Rizzi et al., "On-chip magnetic bead-based DNA melting curve analysis using a magnetoresistive sensor", 2015, J. Magnetism and Magnetic Materials v380, pp. 215-220.

* cited by examiner

| NA | 47.9 | NA | 48.8 | 48.5 | NA | 48.8 | NA | NA | NA |
| 48.6 | 48.5 | 48.7 | 48.2 | 48.8 | 48.9 | 48.8 | 48.3 | 48.5 | 48.3 |
| 48.0 | 48.2 | 48.5 | 48.9 | 48.4 | 48.8 | 48.3 | 48.4 | 48.4 | 48.2 |
| 48.6 | 48.2 | 48.4 | NA | 48.8 | 48.3 | NA | 49.0 | 48.5 | 48.2 |
| 49.0 | 48.6 | 48.7 | 48.6 | 48.5 | 48.4 | 48.1 | 48.3 | 48.4 | 47.6 |
| 49.3 | 49.0 | 49.0 | 48.4 | 48.7 | 48.9 | 48.7 | 48.2 | NA | 48.4 |
| 50.2 | 49.2 | 49.6 | 49.3 | 49.7 | 49.3 | 49.0 | 49.4 | 49.0 | 49.2 |
| 51.4 | 52.6 | 52.4 | 51.7 | 51.6 | 51.3 | 51.7 | 51.0 | 50.2 | 49.5 |

| | | | | | | | | | |
|---|---|---|---|---|---|---|---|---|---|
| 57.6 | 58.0 | 58.3 | 58.5 | 58.6 | 58.7 | 58.5 | 58.3 | 58.1 | 57.8 |
| 57.8 | 58.1 | 58.4 | 58.6 | 58.8 | 58.7 | 58.4 | 58.4 | 58.1 | 57.7 |
| 57.9 | 58.2 | 58.4 | 58.5 | 58.7 | 58.8 | 58.7 | 58.5 | 58.3 | 58.0 |
| 58.0 | 58.4 | 58.6 | 58.9 | 59.0 | 58.9 | 58.5 | 58.3 | 58.2 | 57.9 |
| 57.6 | 58.0 | 58.3 | 58.9 | 59.3 | 59.3 | 59.1 | 58.7 | 58.3 | 57.9 |
| 57.8 | 58.1 | 58.5 | 59.0 | 59.3 | 59.3 | 59.0 | 58.4 | 58.0 | 57.6 |
| 57.6 | 58.0 | 58.4 | 58.8 | 59.1 | 59.2 | 59.0 | 58.6 | 58.2 | 57.9 |
| 57.7 | 58.0 | 58.4 | 58.7 | 59.0 | 59.0 | 58.6 | 58.2 | 57.9 | 57.6 |
| 57.4 | 57.7 | 58.0 | 58.3 | 58.5 | 58.6 | 58.5 | 58.2 | 58.0 | 57.7 |

FIG. 6B

700 performing bisulphite conversion of the DNA strands containing methylated and unmethylated sites to create converted DNA strands with mismatch base pairs

702 performing PCR amplification of the converted DNA strands

704 magnetically labeling single strand target DNA strands among the PCR amplified converted DNA strands

706 hybridizing the magnetically labeled single strand target DNA strands with complementary DNA strands immobilized onto a magnetoresistive (MR) sensor array

708 increasing a stringency condition to cause the magnetically labeled single strand target DNA strands to be denatured from the complementary DNA strands immobilized onto a magnetoresistive (MR) sensor array

710 reading out in real time during the increasing of the stringency condition a denaturation signal resulting from the denatured magnetically labeled single strand target DNA strands

712 determining stringency conditions of methylated and unmethylated DNA strands from the denaturation signal

METHODS FOR ACCURATE TEMPERATURE MEASUREMENT ON GMR BIOSENSOR ARRAYS

CROSS REFERENCE TO RELATED APPLICATIONS

This application claims the benefit of U.S. provisional patent application 62/492,617, filed on May 1, 2017, and hereby incorporated by reference in its entirety.

This application claims the benefit of U.S. provisional patent application 62/659,402, filed on Apr. 18, 2018, and hereby incorporated by reference in its entirety.

FIELD OF THE INVENTION

This invention relates to improved methods for magnetoresistive (MR) biosensing applications.

BACKGROUND

To accurately measure temperature dependent properties of biological interaction (e.g.: DNA melting temperature, affinity, avidity, adsorption and desorption rates etc.), accurate knowledge of the reaction conditions is required. In the particular case of GMR (giant magnetoresistance) biosensor arrays, the working assumption of uniform temperature across the chip area holds true only with the system at thermal equilibrium at room temperature. In every other situation, the inherent shape of the chip and details of the temperature controlling method cause a temperature gradient across the chip surface. Accordingly, it would be an advance in the art to provide improved methods for dealing with temperature measurement and/or calibration in magnetoresistive sensor arrays.

SUMMARY

In an exemplary embodiment, the GMR biosensor chip includes more than 80 GMR resistors distributed in a square array, with a pitch of about 400 µm. The resistivity of the GMR material is linearly dependent on the temperature in the working range 0-100° C. By measuring the resistance of each sensor on the array, it is possible to characterize the temperature gradient across the chip and correct for it in subsequent data analysis.

We provide a method to measure temperature of each sensor by means of a double modulation sensing protocol that allows for synchronous measurement of magnetic nanoparticle binding events (for biosensing) as well as resistivity variation due to temperature. This method can be applied to each sensor individually, thus ensuring two-dimensional quantification of the temperature across the chip. Furthermore, we describe a method to correct for temperature dependency in the sensor sensitivity to magnetic field that would affect the magnetic nanoparticle detection.

DETAILED DESCRIPTION

A) Exemplary Hardware Configuration

Figure 1:
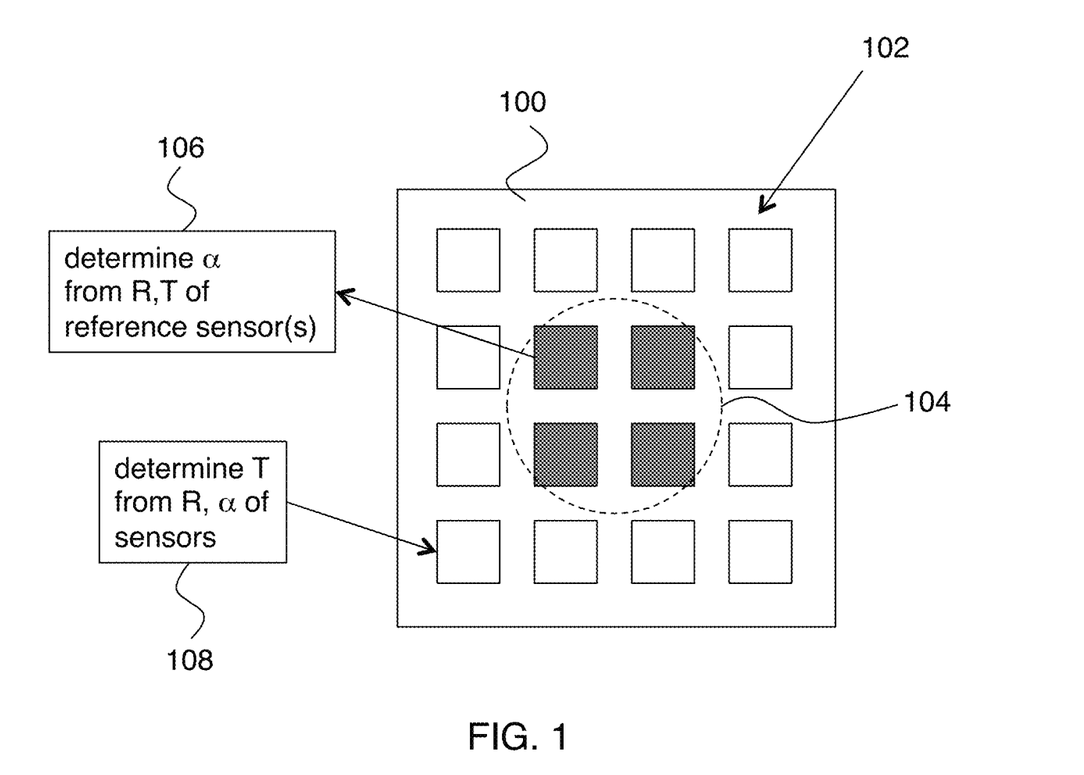
FIG. 1 shows an embodiment of the invention.

FIG. 1 shows an exemplary magnetoresistive sensor array operating in an embodiment of the invention. In this example, an array of magnetoresistive sensors 102 is disposed on a substrate 100, and substrate 100 is disposed on a temperature control member 104. In the top view of FIG. 1, temperature control member 104 is shown with dotted lines because it is in contact with the back side of substrate 100 and therefore is not visible in a top view. As shown on FIG. 1, it is usually the case that some of the magnetoresistive sensors in array 102 are disposed such that they have better thermal contact to temperature control member 104 than the other magnetoresistive sensors. It is convenient to refer to these one or more MR sensors as reference MR sensors. The reference MR sensors on FIG. 1 are shaded. Briefly, the main idea is to use one or more reference sensors to determine the linear temperature coefficient of zero-field resistance, α, by measuring resistance R at two or more known temperatures T (106 on FIG. 1). Once α is known, temperature can be determined from resistance for any sensor in the array (108 on FIG. 1). It is convenient to first consider the implications of double modulation sensing before providing further details of this temperature measurement approach.

B) Double Modulation Sensing

Figure 2:
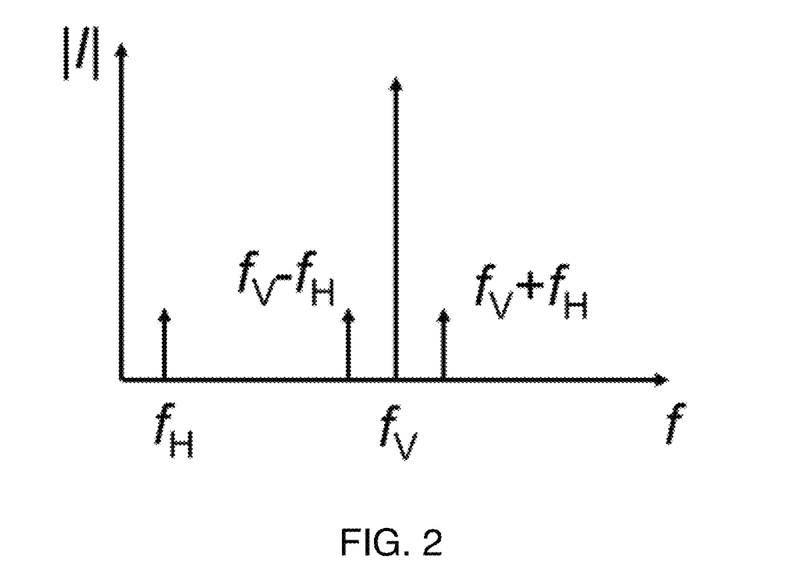
FIG. 2 is a diagram of the idealized output signal in a double modulation sensing system.

GMR sensor are biased with a voltage V at frequency $f_v$. An external magnetic field H is applied at frequency $f_h$. The output signal (i.e. current in the sensor) has ideally 4 main components, as shown on FIG. 2. A center tone (CT) component at frequency $f_v$, two identical side tone (ST) components at $f_v \pm f_h$, and a magnetic pickup noise component induced by the field at $f_h$. Working with $f_v \gg f_h$ it is possible to isolate the signal from the noise at $f_h$ as well as from the 1/f noise. The CT and ST components are detected by spectral analysis. These are found to be:

$$CT = \frac{V}{R_0}, \quad (1)$$

$$ST = -\frac{V \Delta R_0}{4 R_0^2}, \quad (2)$$

where V is the bias voltage, $R_0$ is the zero-field resistance of the sensor and $\Delta R_0$ is the change in resistance when a field H is applied. The figure of merit for magnetoresistive sensor is the magnetoresistive ratio, defined as $MR = \Delta R_0/R_0$. In double modulation sensing the appropriate figure of merit becomes $MR = 4ST/CT$. The magnetoresistive ratio is affected by the presence of magnetic nanoparticles at or near the sensor surface, allowing for biosensing.

C) Temperature Measurement

The resistivity of a GMR sensor depends on temperature, thus, in a double modulation scheme:

$$R(T) = R_0(1 + \alpha \Delta T), \qquad (3)$$

$$CT \sim \frac{V}{R_0}(1 - \alpha \Delta T), \qquad (4)$$

where α is a thermal coefficient that depends on the GMR material but can be assumed constant over the chip. The coefficient α can be obtained by measuring resistances at two known temperatures for one or several reference sensors that are in better thermal contact with the temperature regulation system. If more than one sensor is used, the individual α values can be averaged.

Once the thermal coefficient α is known, we can measure temperature for each sensor on the chip. More explicitly, a method for temperature measurement in an array of magnetoresistive sensors includes the following steps:

1) providing an array of magnetoresistive sensors, where the array of magnetoresistive sensors includes at least one reference magnetoresistive sensor;

2) $R_0$ is a zero field resistivity at a reference temperature $T_0$, T is temperature, α is a material parameter of the magnetoresistive sensors, and the magnetoresistive sensors have a zero field resistivity R given by $$R = R_0(1 + \alpha(T-T_0));$$

3) measuring zero field resistivity of the reference magnetoresistive sensor(s) at two or more known temperatures to determine α; and 4) measuring zero field resistivity of one or more magnetoresistive sensors of the array of magnetoresistive sensors to determine corresponding temperatures T of the one or more magnetoresistive sensors from measured R and known α.

In cases where more than one reference magnetoresistive sensor is employed, determining α can be done by averaging α values of the two or more reference magnetoresistive sensors. Once α is known, temperature can be determined from zero-field resistance for any sensor in the array, whether or not it was used as a reference sensor for determining α.

Figure 3:
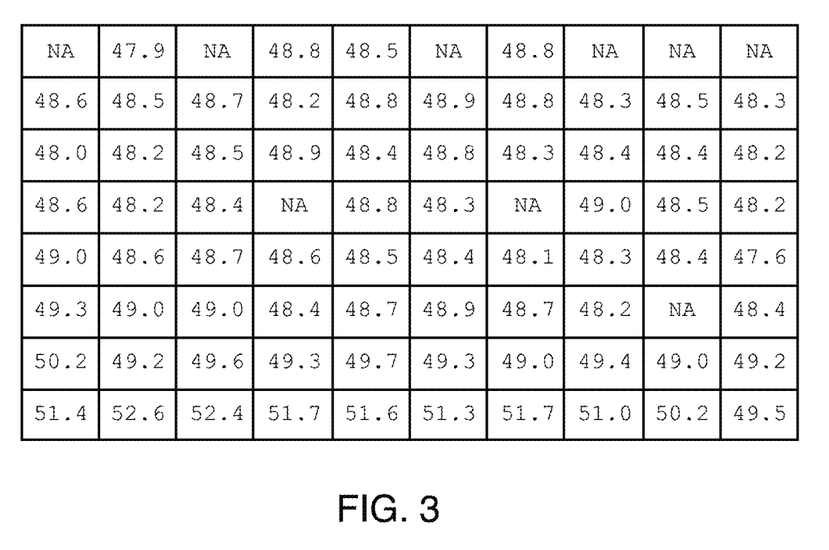
FIG. 3 is a table of measured temperatures from an exemplary magnetoresistive sensor array.

A temperature controlled cartridge used in one embodiment of this invention had a similar configuration to that of FIG. 1. The cartridge was assembled such that the back side of the GMR chip die (i.e., substrate 100) was in thermal contact with the temperature controlled cartridge (i.e., temperature control member 104). The contact area in this case was circular, with a diameter of 1-2 mm. The limited contact area causes a temperature gradient on the chip surface. FIG. 3 shows a temperature distribution across the chip for this example as determined by the above-described method. The temperature varies about 1.5 C from the center to the edge of the chip. The procedure here described allows for accurate temperature measurement of each sensor and for correction for temperature gradients across the GMR chip D) Temperature Correction for Double Modulation Side tone (ST) also depend on temperature, since both the resistivity and the magnetoresistivity of the GMR sensor are temperature dependent. This is normally assumed to be linear for small temperature variation. Thus $$ST \sim -\frac{V \Delta R_0}{4R_0^2}(1 + (\beta - \alpha)\Delta T) \qquad (5)$$

$$CT \sim \frac{V}{R_0}(1 - \alpha \Delta T) \qquad (6)$$

Normalizing CT and ST by their initial values $$\frac{\Delta CT}{CT_0} \sim -\alpha \Delta T \qquad (7)$$

$$\frac{\Delta ST}{ST_0} \sim (\beta - \alpha)\Delta T \qquad (8)$$

From which we obtain $$\frac{\Delta ST}{ST_0} \propto K \frac{\Delta CT}{CT_0} \qquad (9)$$

Thus, CT can be used as an internal temperature measurement to characterize and correct the temperature dependency of ST.

$$1 + (\beta - \alpha)\Delta T = 1 + K \frac{\Delta CT}{CT_0} \qquad (10)$$

$$ST_{corr} = \frac{ST}{1 + K \frac{\Delta CT}{CT_0}} \qquad (11)$$

Figure 4:
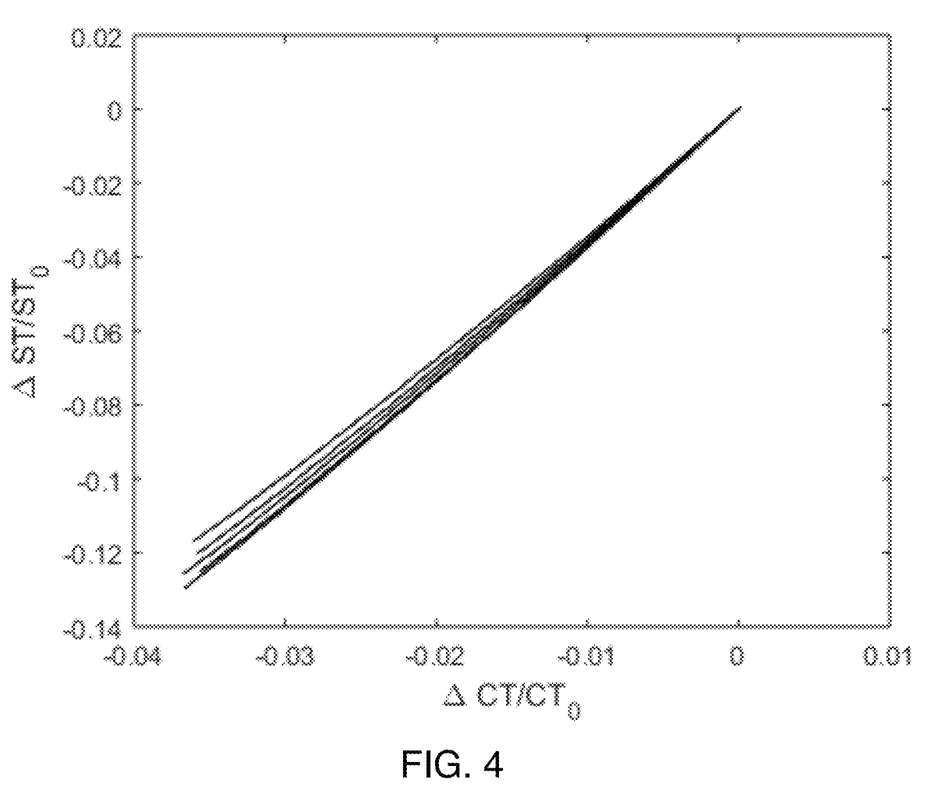
FIG. 4 shows $\Delta ST/ST_0$ vs. $\Delta CT/CT_0$ curves measured for several MR sensors on the chip.

The coefficient K varies across the chip as shown in FIG. 4. More than 10% variation of K was found. The calibration of ST to CT should therefore be performed on each individual sensor.

For small temperature variation of ±10° C., the method presented above is sufficient to correct ST since $\Delta ST/ST_0$ vs. $\Delta CT/CT_0$ can be considered linear. For a larger temperature range, the relation between $\Delta ST/ST_0$ and $\Delta CT/CT_0$ was found to be non-linear. A higher order polynomial ($P_n$) should be fitted to the curve to correct completely the temperature dependency of ST.

$$ST_{corr} = \frac{ST}{1 + P_n\left(\frac{\Delta CT}{CT_0}\right)} \qquad (12)$$

A polynomial of order 3 or higher should be used in those applications in which precise correction of the temperature driven variation is necessary. In one specific case, a polynomial of $5^{th}$ order was identified as the optimal model.

According to these principles, the above described temperature correction methods can further include double modulation according to the following steps:

1) disposing the array of magnetoresistive sensors in a tickling magnetic field having a modulation frequency of $f_h$;

2) providing an electrical excitation to the array of magnetoresistive sensors having a modulation frequency of $f_v$, wherein $f_h$ and $f_v$ are distinct, and where an output spectrum of each magnetoresistive sensor in the array of magnetoresistive sensors includes a carrier tone (CT) at frequency $f_v$ and side tones (STs) at frequencies $f_v \pm f_h$, where the carrier tone has a CT amplitude and the side tones have an ST amplitude;

3) for each magnetoresistive sensor in the array of magnetoresistive sensors, individually determining a baseline relation between the CT amplitude and the ST amplitude in the output spectrum;

4) for each magnetoresistive sensor in the array of magnetoresistive sensors, individually measuring corresponding CT and ST amplitudes when a sample is present to provide an input CT measurement and an input ST measurement;

5) for each magnetoresistive sensor in the array of magnetoresistive sensors, individually correcting the input ST measurement using the corresponding baseline relation and the corresponding input CT measurement to provide a corresponding corrected ST measurement (e.g., according to Eq. 11 for a linear correction and according to equation 12 for a polynomial fit correction); and 6) for each magnetoresistive sensor in the array of magnetoresistive sensors, individually providing the corrected ST measurement as an output.

The baseline relation between CT amplitude and ST amplitude can be determined individually for each sensor in the array by collecting ST vs. CT data for each sensor and determining a corresponding curve fit to that ST vs. CT data. The result is curve fits individually corresponding to each sensor in the array. As indicated above, these curve fits can be linear fits and/or higher order polynomial curve fits.

E) Application to Biological Assays

Biological assays are an important application of the present methods. Here we consider DNA melting curve measurements as an example of temperature sensitive biological measurement. In this example, a magnetic labeled single stranded DNA target is hybridized to surface tethered single stranded DNA probes. After binding, the temperature is raised and a melting curve is measured while the temperature is increased.

Figure 5A:
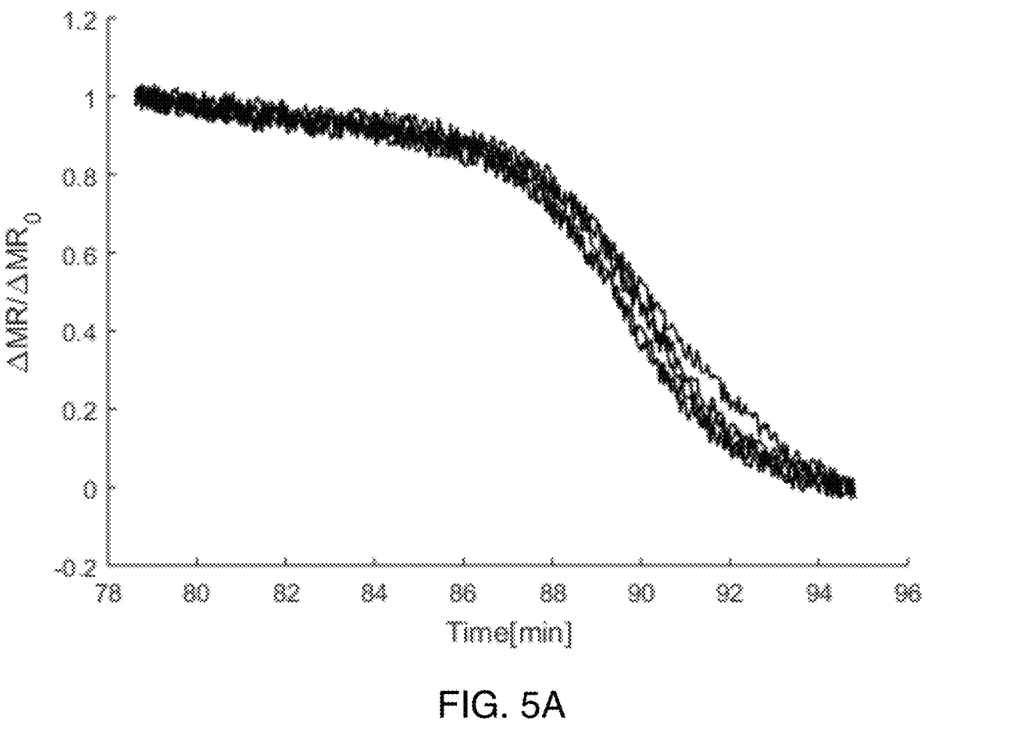
FIG. 5A shows DNA signal vs. time during a temperature ramp at 0.05 C/s for several MR sensors on the chip.
Figure 5B:
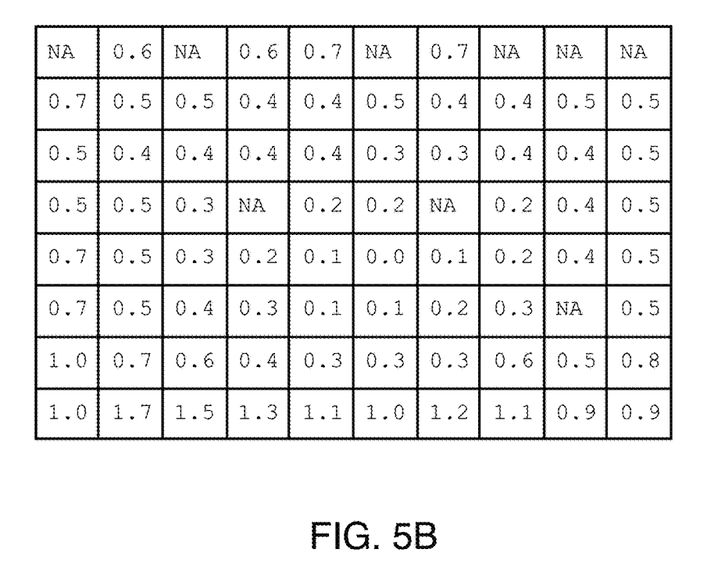
FIG. 5B is a table of melt delay in minutes for each sensor in the array, relative to the first sensor on the chip to melt (at row 5, column 6).

FIG. 5A shows the time series for such a melting. A sigmoid fit was applied to the curves to calculate the time of melt for each sensor. The relative time delay results are shown in the table of FIG. 5B. The central sensors in FIG. 5B are at a higher temperature and thus melt the DNA hybrids earlier. A melting time difference of 0.7 min corresponds to a temperature difference of 2.1 C that must be accounted for.

Figure 6A:
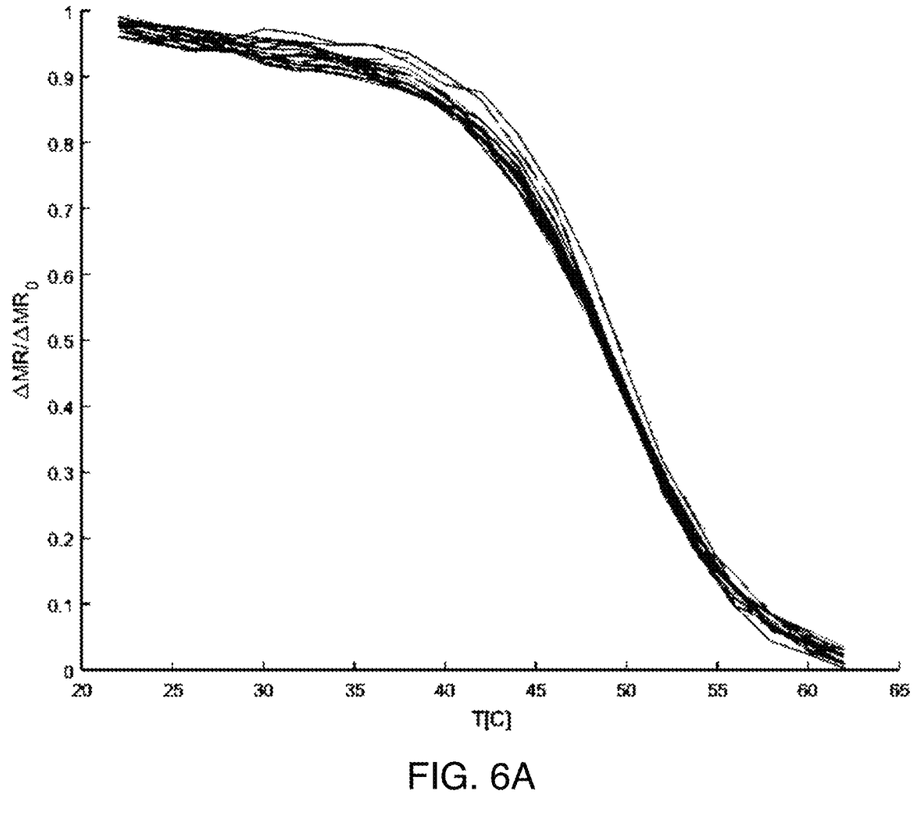
FIG. 6A shows melting curves from sensors in rows 2-4 after temperature calibration.
Figure 6B:
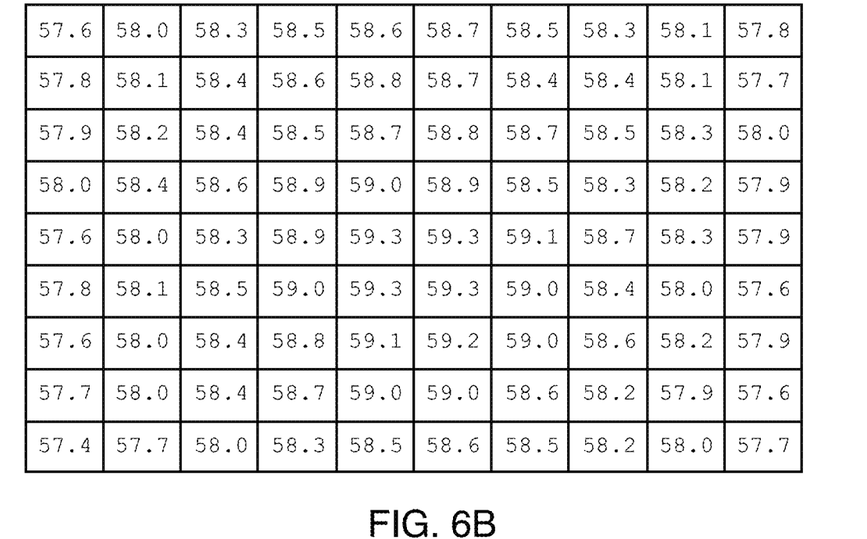
FIG. 6B is a table of melting temperature measured on each sensor after temperature calibration.

Using the temperature measured for each sensor as described above, we can provide this correction, as shown on FIGS. 6A-B. In FIG. 6A, the measured melting curves are similar to each other after this temperature correction and calibration. FIG. 6B shows the melting temperature obtained by sigmoid fitting. The measured melting temperature for rows 1-5 vary less than 1 C. The other rows are affected by the wiring and epoxy potting in this particular case.

According to these principles, the above described temperature correction and double modulation methods can further include biological assays where the sample includes analytes labeled with magnetic nanoparticles and where one or more of the magnetoresistive sensors has capture reagents disposed thereon corresponding to the analytes, such that binding and immobilization of analytes with corresponding capture reagents provides a magnetoresistive assay.

More specifically, an exemplary assay according to this approach has the analytes and capture species being complementary DNA strands, and further includes the following steps:

1) performing bisulphite conversion of DNA strands containing methylated and unmethylated sites to create converted DNA strands with mismatched base pairs;

2) performing polymerase chain reaction (PCR) amplification of the converted DNA strands;

3) magnetically labeling single strand target DNA strands among the PCR amplified converted DNA strands;

4) hybridizing the magnetically labeled single strand target DNA strands with complementary DNA strands immobilized onto the magnetoresistive sensor array;

5) increasing a stringency condition to cause the magnetically labeled single strand target DNA strands to be denatured from the complementary DNA strands immobilized onto the magnetoresistive sensor array;

6) reading out in real time during the increasing of the stringency condition a denaturation signal resulting from the denatured magnetically labeled single strand target DNA strands; and 7) determining stringency conditions of methylated and unmethylated DNA strands from the denaturation signal.

In this approach, the denaturation signal can be combined with the corresponding magnetoresistive sensor temperature T to individually provide accurate DNA melting curves for each magnetoresistive sensor, as in the examples of FIGS. 6A-6B above.

E1) Further Details on Biological Assay Applications

Figure 7:
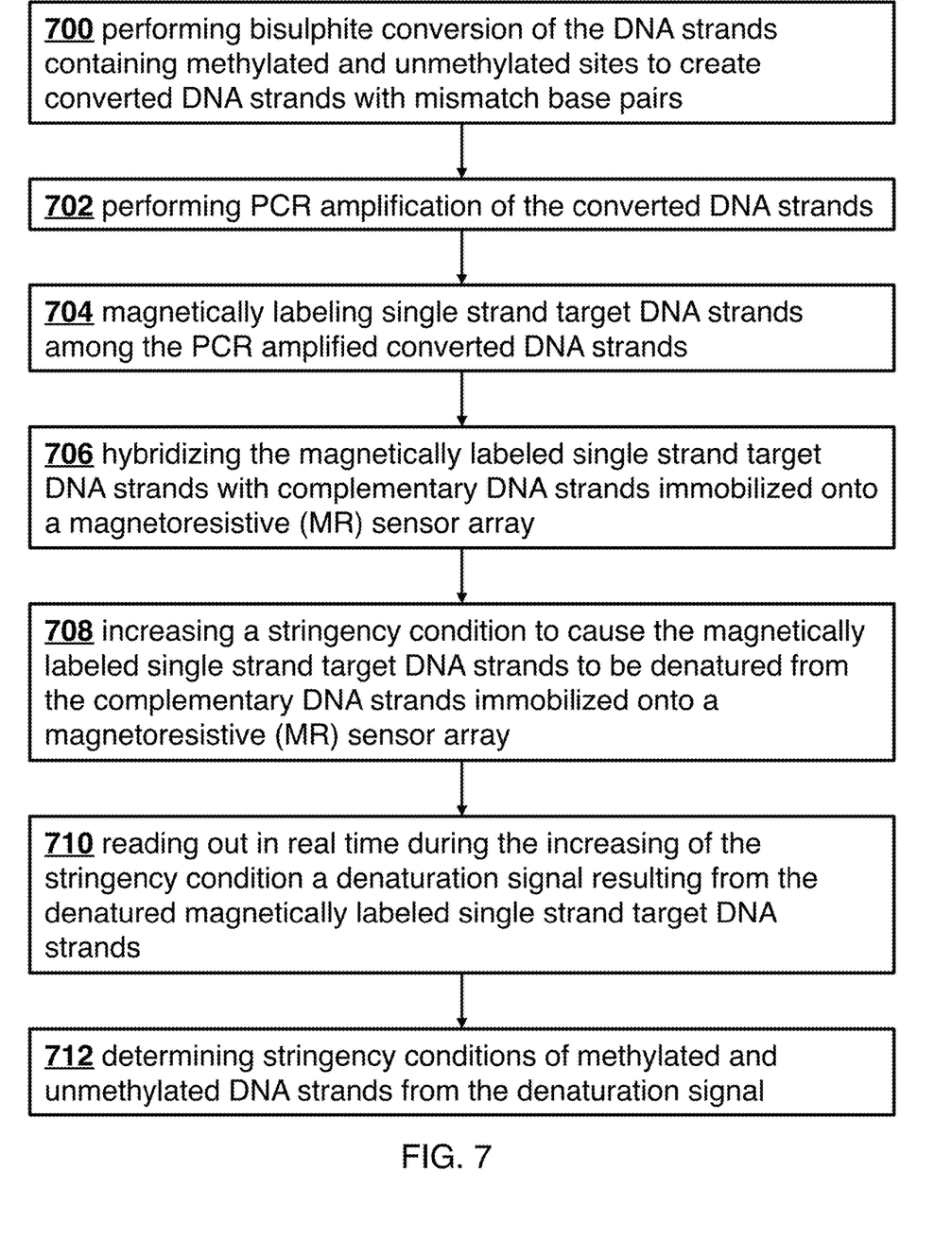
FIG. 7 is a flow diagram of an assay suitable for practice in connection with embodiments of the invention.

FIG. 7 is a flow chart providing an overview of a method of methylation detection providing a quantitative description of the methylation density in DNA strands. In step 700, bisulphite conversion of the DNA strands containing methylated and unmethylated sites is performed to create converted DNA strands with mismatch base pairs. In step 702, PCR amplification of the converted DNA strands is performed. In step 704, single strand target DNA strands among the PCR amplified converted DNA strands are magnetically labeled. In step 706, the magnetically labeled single strand target DNA strands are hybridized with complementary DNA strands immobilized onto a magnetoresistive (MR) sensor array. In some implementations, during hybridizing a binding signal is read out in real time.

In step 708, a stringency condition is increased to cause the magnetically labeled single strand target DNA strands to be denatured from the complementary DNA strands immobilized onto a magnetoresistive (MR) sensor array. In step 710, during the increasing of the stringency condition a denaturation signal resulting from the denatured magnetically labeled single strand target DNA strands is read out in real time. In step 712, stringency conditions of methylated and unmethylated DNA strands are determined from the denaturation signal.

The stringency condition may be temperature, in which case increasing the stringency condition comprises increasing the temperature while salt concentration is held constant. Determining the stringency conditions of the methylated and unmethylated DNA strands in this case comprises determining melting temperatures of the methylated and unmethylated DNA strands. Alternatively, the stringency condition may be salt concentration, in which case increasing the stringency condition comprises decreasing the salt concentration while temperature is held constant. Determining the stringency conditions of the methylated and unmethylated DNA strands in this case comprises determining melting salt concentrations of the methylated and unmethylated DNA strands.

In some implementations, the method may be used to determine mutation sites simultaneously with methylation sites. In this case, performing bisulphite conversion of the DNA strands containing methylated and unmethylated sites includes performing bisulphite conversion of the DNA strands containing methylated and unmethylated sites and wild type genes and mutated genes. In addition, determining stringency conditions of methylated and unmethylated DNA strands from the denaturation signal in this case includes determining stringency conditions of methylated and unmethylated DNA strands and wild type genes and mutated type genes from the denaturation signal.

Figure 8:
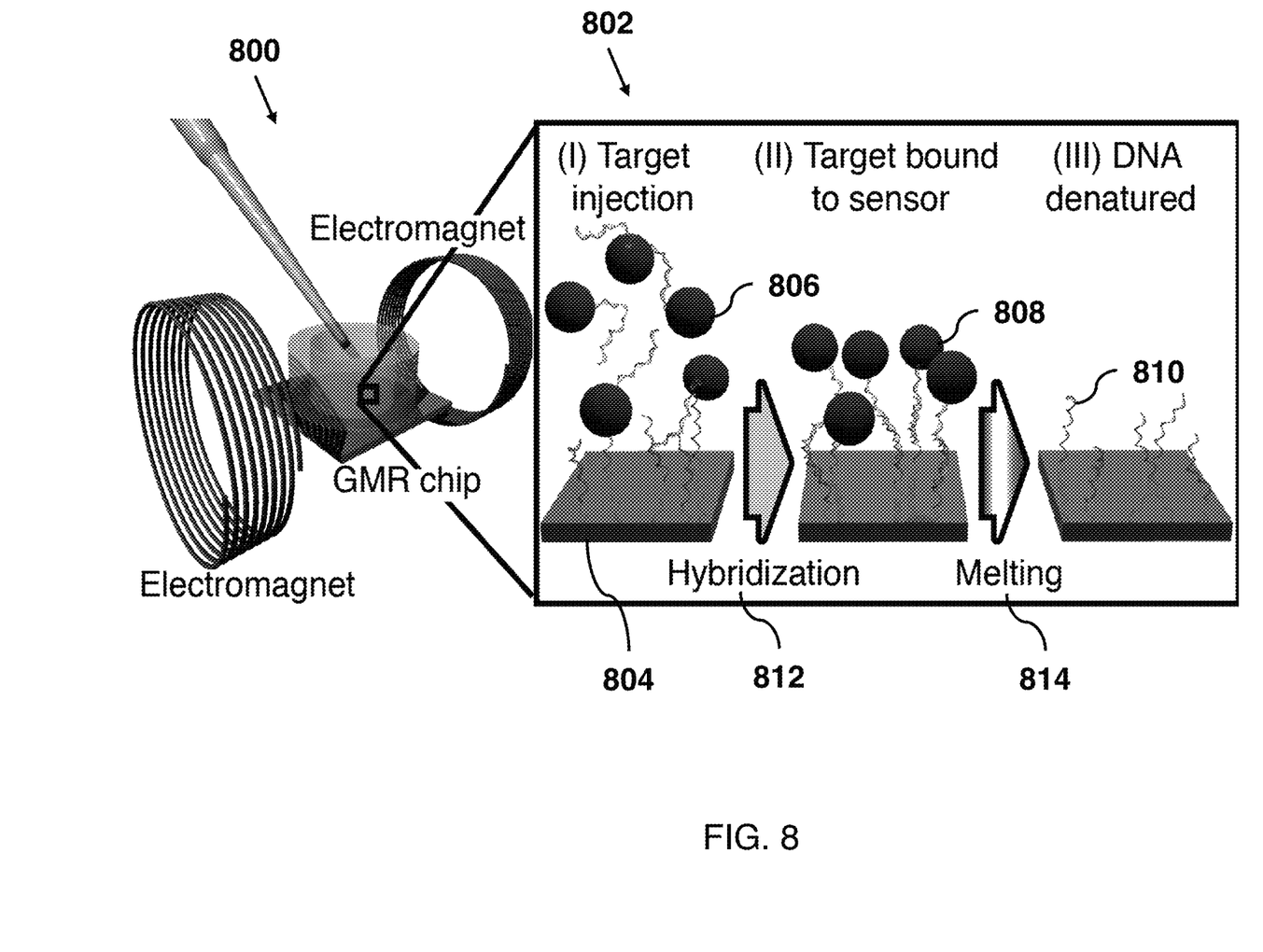
FIG. 8 shows an exemplary apparatus for carrying out the assay of FIG. 7.

FIG. 8 provides a schematic overview of a protocol 802 for the detection of magnetically labeled DNA using a GMR biosensor device 800. After denaturation of the reverse strand and labeling, PCR products are injected into the reaction well over the chip 804. In a hybridization step 812, DNA labeled with MNPs (magnetic nanoparticles) 806 hybridizes to complementary surface-tethered probes for 1 hour at 37° C., resulting in hybridized DNA labeled with MNPs 808. Unbound sample is removed by washing. In melting step 814, the temperature is swept from 20° C. to 65° C., causing denaturation of the DNA from the probes 810 to measure the melting temperature, $T_m$.

To detect DNA mutations, we PCR amplified the genomic regions of interest using non-discriminatory primers. The PCR products were then magnetically labeled using biotinylated primers and streptavidin-coated magnetic nanoparticles (MNPs). After magnetic column separation and denaturation of the double-stranded PCR products, ssDNA conjugated to MNPs (MNP-ssDNA) was introduced to the GMR biosensor array where multiple DNA probes were separately tethered to the surface of each sensor. Upon hybridization of the injected MNP-ssDNA to surface-tethered complementary probes, GMR biosensors produced changes in sensor magnetoresistive ratio (ΔMR) proportional to the bound MNPs. To genotype a mutation, we employed a set of two probes complementary to the wild type (WT) and mutant type (MT) sequences of the sample. During hybridization at low stringency, amplicons hybridized to both WT and MT probes with similar affinity. To obtain single base specificity, stringent washing is typically used after hybridization in DNA microarray. To achieve a more flexible system for detection of single-base mutations, we challenged the hybrids by increasing the temperature and continuously measuring DNA melting simultaneously for all probes on the GMR biosensor array.

Figure 9A:
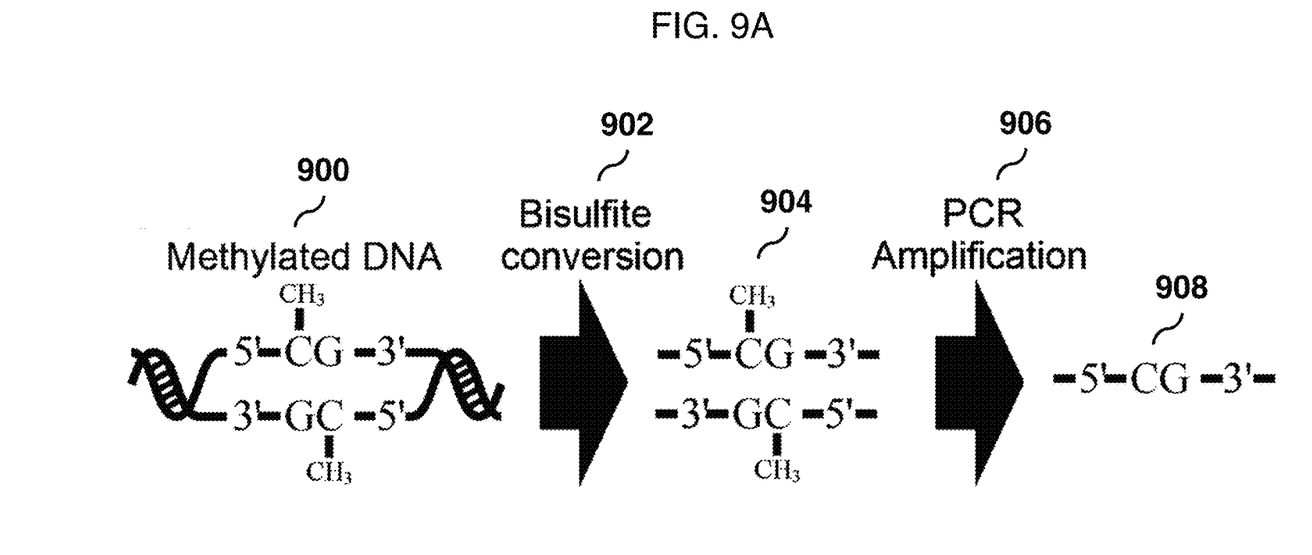
FIGS. 9A-B show further details relating to the assay of FIG. 7.
Figure 9B:
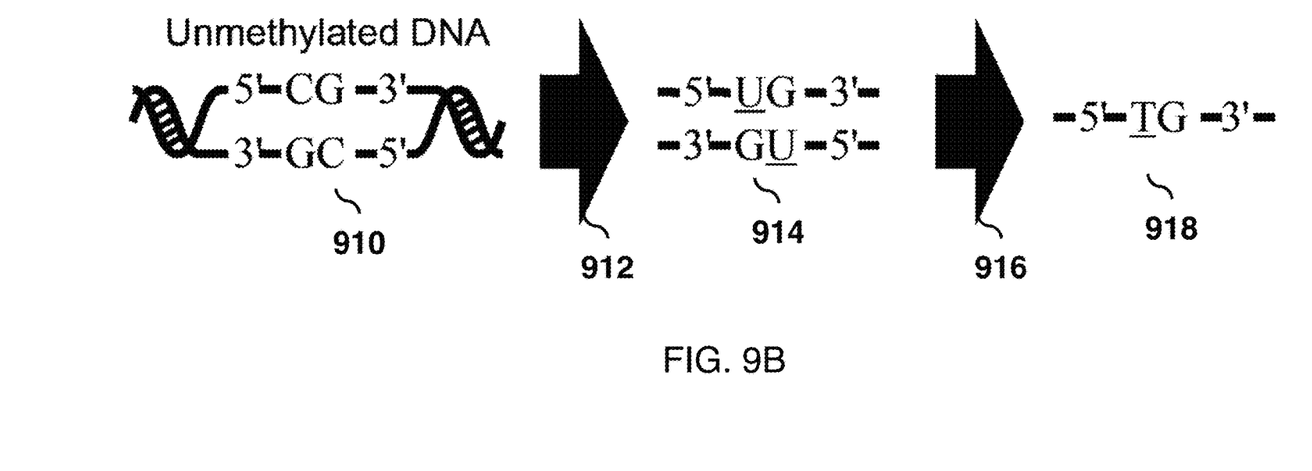

FIGS. 9A-B are schematic illustrations of the bisulphite conversion process. Upon bisulphite treatment 902, 912, unmethylated cytosines in DNA 910 are converted to uracil in DNA 914 (FIG. 9B) whereas 5-methylcytosines in DNA 900 are retained in DNA 904 (FIG. 9A). In the subsequent PCR 906, 916, which produces products 908, 918, uracil in 914 is substituted by thymine. Thus, the methylated cytosines are mapped to single base alterations (C>T) of the amplicons.

The invention claimed is:

1. A method for temperature measurement of an array of magnetoresistive sensors, the method comprising:
providing an array of magnetoresistive sensors, wherein the array of magnetoresistive sensors includes at least one reference magnetoresistive sensor;
wherein $R_0$ is a zero field resistivity at a reference temperature $T_0$, wherein T is temperature, wherein α is a material parameter of the array of magnetoresistive sensors, and wherein each magnetoresistive sensor of the array of magnetoresistive sensors has a zero field resistivity R given by $R=R_0 (1+\alpha (T-T_0))$;
measuring zero field resistivity R of the at least one reference magnetoresistive sensor at two or more known temperatures T to determine α;
measuring zero field resistivity R of one or more magnetoresistive sensors of the array of magnetoresistive sensors to determine corresponding temperatures T of the one or more magnetoresistive sensors from measured R and known α;
wherein the one or more magnetoresistive sensors of the array of magnetoresistive sensors include at least one magnetoresistive sensor of the array of magnetoresistive sensors that is not a reference magnetoresistive sensor.

2. The method of claim 1, wherein there are two or more reference magnetoresistive sensors, and wherein determining α comprises averaging α values of the two or more reference magnetoresistive sensors.

3. The method of claim 1, further comprising
disposing the array of magnetoresistive sensors in a tickling magnetic field having a modulation frequency of $f_h$;
providing an electrical excitation to the array of magnetoresistive sensors having a modulation frequency of $f_v$, wherein $f_h$ and $f_v$ are distinct, and wherein an output spectrum of each magnetoresistive sensor in the array of magnetoresistive sensors includes a carrier tone (CT) at frequency $f_v$ and side tones (STs) at frequencies $f_v \pm f_h$, wherein the carrier tone has a CT amplitude and the side tones have an ST amplitude;
for each magnetoresistive sensor in the array of magnetoresistive sensors, individually determining a baseline relation between the CT amplitude and the ST amplitude in the output spectrum;
for each magnetoresistive sensor in the array of magnetoresistive sensors, individually measuring corresponding CT and ST amplitudes when a sample is present to provide an input CT measurement and an input ST measurement;
for each magnetoresistive sensor in the array of magnetoresistive sensors, individually correcting the input ST measurement using the corresponding baseline relation and the corresponding input CT measurement to provide a corresponding corrected ST measurement; and
for each magnetoresistive sensor in the array of magnetoresistive sensors, individually providing the corrected ST measurement as an output.

4. The method of claim 3, wherein the individually determining a baseline relation between CT amplitude and ST amplitude comprises collecting ST vs. CT data for each magnetoresistive sensor in the array of magnetoresistive sensors followed by determining a curve fit relating baseline ST amplitude to baseline CT amplitude for each magnetoresistive sensor in the array of magnetoresistive sensors.

5. The method of claim 4, wherein for one or more of the magnetoresistive sensors in the array of magnetoresistive sensors, the curve fit is a linear fit.

6. The method of claim 4, wherein for one or more of the magnetoresistive sensors in the array of magnetoresistive sensors, the curve fit is a polynomial fit.

7. The method of claim 6,
wherein the sample includes analytes labeled with magnetic nanoparticles, and
wherein one or more magnetoresistive sensors of the array of magnetoresistive sensors has capture reagents disposed thereon corresponding to the analytes, whereby binding and immobilization of analytes with corresponding capture reagents provides a magnetoresistive assay.

8. The method of claim 7, further comprising combining an assay signal of the magnetoresistive assay with the corresponding magnetoresistive sensor temperature T to individually provide accurate assay curves for each magnetoresistive sensor.

9. The method of claim 8 wherein the assay signal is a DNA denaturation signal and wherein the assay curve is a DNA melting curve.

10. The method of claim 3,
wherein the sample includes analytes labeled with magnetic nanoparticles, and
wherein one or more magnetoresistive sensors of the array of magnetoresistive sensors has capture reagents disposed thereon corresponding to the analytes, whereby binding and immobilization of analytes with corresponding capture reagents provides a magnetoresistive assay.

11. The method of claim 10, further comprising combining an assay signal of the magnetoresistive assay with the corresponding magnetoresistive sensor temperature T to individually provide accurate assay curves for each magnetoresistive sensor.

12. The method of claim 11 wherein the assay signal is a DNA denaturation signal and wherein the assay curve is a DNA melting curve.

* * * * *